United States Patent [19]

Olsen

[11] Patent Number: 4,837,029
[45] Date of Patent: Jun. 6, 1989

[54] LOW FOAMING, AQUEOUSLY HOMOGENIZABLE RIFAMPIN COMPOSITION

[75] Inventor: James L. Olsen, Chapel Hill, N.C.

[73] Assignee: Carolina Medical Products, Inc., Chapel Hill, N.C.

[21] Appl. No.: 34,767

[22] Filed: Apr. 6, 1987

[51] Int. Cl.4 .................. A61K 9/48; A61K 31/74
[52] U.S. Cl. .................. 424/451; 424/464; 424/78; 514/255
[58] Field of Search .................. 424/78, 451, 464

[56] References Cited

U.S. PATENT DOCUMENTS

| | | | |
|---|---|---|---|
| 4,195,084 | 3/1980 | Ong ........................... | 514/937 |
| 4,332,789 | 6/1982 | Mlodozeniec ............... | 424/443 |
| 4,613,496 | 9/1986 | Kopf ........................... | 514/255 |
| 4,687,662 | 8/1987 | Schobel ...................... | 514/159 |

*Primary Examiner*—Joseph L. Schofer
*Assistant Examiner*—Peter F. Kulkosky
*Attorney, Agent, or Firm*—Lynn E. Barber; Steven J. Hultquist

[57] ABSTRACT

An antibiotic composition comprising rifampin, a dimethyl polysiloxane polymer, and a cationic or nonionic surfactant, wherein the rifampin, dimethyl polysiloxane polymer, and surfactant are present in relative amounts such that the composition is aqueously homogenizable with low foaming.

Also disclosed is a method of antibiotic treatment wherein such composition is administered orally, either in a solid dosage form or in an aqueous medium.

20 Claims, No Drawings

LOW FOAMING, AQUEOUSLY HOMOGENIZABLE RIFAMPIN COMPOSITION

BACKGROUND OF THE INVENTION

1. Field of the Invention

This invention relates generally to antibiotic compositions comprising rifampin, of a type which is orally administerable, and particularly to a composition of such type which is aqueously homogenizable with low foaming.

2. Description of the Related Art

Rifampin is a semi-synthetic antibiotic which has been widely used in pharmaceutical applications, particularly as an antibacterial and antitubercular compound.

Although highly useful as an antibiotic in these application areas, rifampin has the inherent disadvantage that it is poorly soluble in water, being only slightly soluble at a pH below 6. As a result, the physiological availability of such compound, especially at the higher pH values present in the lower gastrointestinal system, is poor.

This solubility problem has been recognized in the art, and various additives have been proposed to overcome such deficiency, as noted in U.S. Pat. No. 4,613,496 to Helmut Kopf, et al, with reference to Japanese Patent Disclosure No. SHO 53-1333624 of Nov. 21, 1978. Among the additives described in the Japanese reference for overcoming such poor solubility characteristics are sodium lauryl sulfate, a sucrose fatty acid ester, a sorbitan fatty acid ester, dioctyl sulfosuccinate, fillers such as lactose, D-mannitol, and corn starch, and lubricants such as calcium stearate. The resulting compositions are said by the U.S. patent to exhibit unsatisfactory to poor elution properties at a pH of 3.

Also described in the U.S. patent to Kopf et al are mixtures of rifampin with crystalline cellulose, alone or with polyoxylol 40 stearate, polysorbate 80, glycerol monostearate, hydroxypropyl cellulose, or hydroxypropyl methylcellulose, with magnesium stearate present in all instances as a lubricant. Such mixtures are disclosed as having satisfactory elution properties at a pH of 3.

The specific improvement in rifampin soluble compositions in U.S. Pat. No. 4,613,496 is the provision of a composition containing a mixture of from about 75 to about 90 percent of rifampin, from about 5 to about 20 percent of crystalline cellulose, about 0.05 to about 5 percent of sodium lauryl sulfate, and about 0.5 to about 5 percent of a pharmaceutically acceptable lubricant, e.g., magnesium stearate. Such composition is disclosed as having uniform and complete dissolution rates in both acidic media simulating the conditions of the normal and healthy human stomach and the neutral to slightly basic medium simulating abnormal human stomach conditions, as well as those of the lower gastrointestinal tract. As a result, the disclosed composition of this patent is said therein to exhibit a dissolution rate which is virtually independent of the surrounding pH conditions and which guarantees a consistently uniform and for all practical purposes a complete availability of the active ingredient (rifampin).

The rifampin composition disclosed in the above-described Kopf et al patent is described as a solid pharmaceutical composition primarily useful for oral administration, e.g., in the form of an uncoated or coated tablet, or a capsule.

While the rifampin composition disclosed in the Kopf et al patent is described as having superior overall elution characteristics in the analytical test (column dissolution rate test) referenced at column 2, lines 26-33 of the patent, as simulative of physiological environments in which the drug may be employed, it nonetheless is true that in vivo the rifampin in aqueous physiological media will have a high degree of foaming character, and such foaming will significantly adversely affect the bioavailability of rifampin therein.

It therefore is an object of the present invention to provide a rifampin composition which is aqueously homogenizable with low foaming.

It is another object of the invention to provide such a composition in a form which is orally administerable, either in solid form such as tablets or capsules, or in an aqueous carrier medium.

It is a further object of the invention to provide a method of antibiotic treatment using such rifampin composition.

Other objects and advantages will be more fully apparent from the ensuing disclosure and appended claims.

SUMMARY OF THE INVENTION

In one aspect, the invention relates to an antibiotic composition comprising rifampin, a dimethyl polysiloxane polymer, and a pharmaceutically acceptable cationic or nonionic surfactant, wherein the rifamin, dimethyl polysiloxane polymer, and pharmaceutically acceptable cationic or nonionic surfactant, are each present in amounts such that the composition is aqueously homogenizable with low foaming incident thereto.

In another aspect, the invention relates to an antibiotic composition consisting essentially of a mixture of from about 1 to 99 percent by weight rifampin, from about 0.05 to about 10 percent by weight of a pharmaceutically acceptable antifoam material, and from about 0.01 to about 5 percent by weight of a pharmaceutically acceptable cationic or non-ionic surfactant.

In a still further aspect, the invention relates to a method of antibiotic treatment of a mammal, comprising administering to such mammal an antibiotically effective amount of a composition as described above.

Other features and embodiments of the invention will be more fully apparent from the ensuing disclosure and appended claims.

DETAILED DESCRIPTION OF THE INVENTION, AND PREFERRED EMBODIMENTS THEREOF

As indicated hereinabove in the "Background of the Invention" section, rifampin by itself in an aqueous medium has poor wetting character, and produces considerable foam when mixed in such aqueous medium.

As a result, rifampin in an aqueous medium, e.g., water or an aqueous syrup, forms a lumpy, foamy poor suspension, which is ill-suited for pharmaceutical use. Upon ingestion by humans as a dosage form, absorption of the rifampin would not be expected to be complete because of the non-wetted, foamy character of the mixture.

The present invention is based on the discovery that these adverse characteristic can be substantially completely overcome by utilizing the rifampin in combination with (1) a dimethyl polysiloxane polymer, and (2) a surfactant which is either cationic or non-ionic in character. The resulting antibiotic composition, when added to or incorporated in water, an aqueous syrup, or other aqueous vehicles, or which when incorporated in a solid dosage form, such as a capsule or tablet, and subsequently ingested will form a low-foaming and uniform mix in the aqueous medium.

This combination of low-foaming character and good wetting properties is particularly surprising, in view of the fact that rifampin with the dimethyl polysiloxane polymer alone will reduce the foaming character of the rifampin in aqueous medium, but the rifampin will still not wet uniformly or smoothly. The use of rifampin with a surfactant alone will improve wetting properties of the active ingredient, but will generate even more foam than would otherwise be generated by the rifampin per se. Surprisingly, however, the addition of both the dimethyl polysiloxane polymer and the cationic or non-ionic surfactant to the rifampin in appropriate amounts, overcomes both the wetting and foaming problems otherwise associated with the active ingredient. In this respect, it is to be noted that addition of a surfactant material to a pharmaceutical composition which is foaming in character, is logically expected to exacerbate the foaming problem, since surfactants are in themselves productive of foaming behavior.

Only relatively small quantities of the dimethyl polysiloxane polymer and the surfactant as compared to the amount of rifampin present, are required in the compositions of the invention.

Broadly speaking, the compositions according to the present invention comprise rifampin in an amount rendering it pharmaceutical available when administered, with the dimethyl polysiloxane polymer being present in an amount which is antifoamingly effective for the composition, to produce low-foaming character in an aqueous medium, and with the surfactant being present in an amount which does not overwhelm the antifoaming capability of the dimethyl polysiloxane polymer, and which is effective to impart suitable wetting behavior to the composition.

In general, these criteria are met in an antibiotic composition comprising rifampin in an amount of from about 1 to about 99 percent by weight, dimethyl polysiloxane polymer in an amount of from about 0.05 to about 10 percent by weight, and the cationic or non-ionic surfactant in an amount of from about 0.01 to about 5 percent by weight, and wherein the weight percentages of the respective components total to 100 percent.

The rifampin which is employed as the active ingredient of the compositions according to the present invention is 5, 6, 9, 17, 19, 21-hexahydroxy-23-methoxy-2, 4, 12, 16, 18, 20, 22-heptamethyl-8-[N-(4-methyl-1-piperazinyl) formimidoyl]-2, 7-(epoxypentadecal[1, 11, 13] trienimino) naphtho (2, 1-b]furan-1, 11 (2H)-dione 21-acetate, sometimes alternatively referred to as rifampicin. This active ingredient is suitably used in compositions according to the present invention in its typical crystalline form.

The dimethyl polysiloxane polymer which usefully may be employed in the composition of the invention preferaby has the formula:

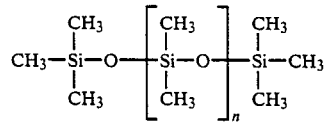

wherein n is from about 200 to about 350. Such polymer may suitably be provided as a mixture of dimethyl polysiloxanes of such type and silica gel which has been purified for pharmaceutical use. A particularly preferred dimethyl polysiloxane/silica gel mixture is simethicone, commercially available under the trade name "Medical Antifoam A" from Dow-Corning, Midland, Mich. Another useful simethicone material is "Medical Antifoam AF Emulsion" (Simethicone Emulsion USP), a 30 percent emulsion of simethicone available from the same manufacturer.

The surfactant usefully employed in rifampin compositions according to the prsent invention is either cationic non-ionic in character. The surfactant may be any suitable cationic or non-ionic material having surfactant activity, which is compatible with the composition, effective to provide wettability when used in the selected amount in the composition, and does not preclude efficacy of the active ingredient rifampin for its intended purpose.

Useful cationic surfactants include dioctyl sodium sulfosuccinate and related surfactant compounds. The preferred dioctyl sodium sulfosuccinate is commercially available as docusate sodium USP. The dioctyl sodium sulfosuccinate may be employed in combination with suitable additives, e.g., preservatives; an example is DSS Granular surfactant (Mallinckrodt Company, St. Louis, Mo.), a combination of docusate sodium USP, 85 percent by weight, and potassium benzoate as a preservative against mold and yeast contamination, and present at 15 percent by weight. Such DSS Granular product is particularly advantageous in the practice of the present invention, since it is a powder useful for absorbing the preferred simethicone constituent, which is a viscous liquid and therefore difficult to mix uniformly.

Non-ionic surfactants which may be employed in the rifampin compositions of the invention include any suitable surfactant materials having non-ionic character which are compatible with the constituents of the composition, and do not negate the efficacy of the active ingredient rifampin. A preferred non-ionic surfactant is polysorbate 20, commercially available as Tween 20 (ICI Americas Company, Wilmington, Del.), and other non-ionic surfactants available under such trade name (Tween) from the same supplier.

The rifampin compositions of the invention may, in one embodiment, consist essentially of the rifampin, dimethyl polysiloxane polymer, and surfactant components, as a solid mixture which may be orally administered in a solid dosage form, e.g., a capsule or tablet. Such solid dosage form is aqueously homogenizeable, i.e., in aqueous medium it forms a readily uniformly dispersible and wettable material, with low foaming. Accordingly, the solid dosage form when ingested will uniformly mix with the aqueous gastrointestinal medium, with low foaming.

Alternatively, such solid mixture of rifampin, dimelthyl polysiloxane polymer, and surfactant may be added to, or incorporated in, a pharmaceutically acceptable aqueous vehicle, i.e, carrier medium. Suitable carriers include water per se, as well as water-based liquid syrups. In such liquid formulations, the composition may employ any suitable additives or additional components, such as colors, flavors, preservatives, suspending agents, and any other materials which may advantageously be employed, and which do not preclude the efficacy of the rifampin in the formulation.

In like manner, the solid powdered mixture of the present reconstitution in aqueous medium at the time of dispensing, e.g., by a pharmacist. For such purpose, the powdered mixture composition comprising rifampin, dimethyl polysiloxane polymer and surfactant, may additionally comprise suitable coloring and flavoring additives, and fillers which enhance the flowability of the solid mixture, provide an adsorbent medium for the viscous liquid dimethyl polysiloxane polymer constituent, etc.

Illustrative fillers for such purpose may include crystalline cellulose materials, such as those described in the aforementioned Kopf, et al patent. A preferred crystalline cellulose material is methylcellulose A4C, commercially available from The Dow Chemical Co., Midland, Mich. Other suitable filler materials include colloidal silicon dioxide, such as Cab-O-Sil silicon dioxide (Cabot Corporation, Boston, Mass.), a fumed silica sub-micron particle sized material (colloidal silicon dioxide NF).

Compositions according to the present invention, in the various dosage forms described above, are orally administerable to mammalian subjects, e.g, humans, for antibiotic treatment in applications where rifampin is usefully employed, e.g., as an antibacterial or antitubucular treatment.

Relative to prior art solid dosage forms of rifampin, the compositions of the present invention display faster and more extensive dissolution in aqueous media, indicating that higher blood levels of the active ingredient rifampin are achievable in vivo from oral administration of the rifampin compositions of the invention, as opposed to the rifampin solid dosage forms previously employed.

The features and advantages of the present invention are more fully shown with the respect to the following non-limiting examples, wherein all parts and percentages are by weight, unless otherwise expressly specified.

EXAMPLE I 300 mg of rifampin powder was added to 50 ml of Purified Water USP in a 2 oz prescription bottle, and the bottle shaken The rifampin did not wet well, leaving clumps of powder on top of the suspension and sticking to the glass. The suspension also produced about one-half inch height of foam on top of the liquid, making the suspension further unacceptable pharmaceutically. The suspension was red in color.

EXAMPLE II

The procedure of Example I was repeated, with the addition of 20 mg of DSS Granular. The rifampin wet well and this resulted in a uniform suspension without lumps, a more pharmaceutically acceptable product since dissolution and absorption of the active ingredient would thereby be enhanced. The suspension, however, formed a dense foam of about one inch height on top of the liquid, again rendering the product unacceptable. The suspension was red in color.

EXAMPLE III

The procedure of Example 1 was repeated with the addition of 50 mg of Simethicone USP. After the bottle was shaken there was no foam as in the previous examples, however the rifampin powder did not wet well, clumped on top and against the glass surface. This combination would not be pharmaceutically acceptable because the clumping and non-wetted powder would not be available for dissolution and absorption by the body. The suspension was red in color.

EXAMPLE IV

The procedure of Example 1 was repeated with the addition of both 20 mg of DSS Granular and 50 mg of Simethicone. The powdered rifampin wet well and formed a uniform suspension without much agitation. Upon shaking, the suspension formed only slight foam, which quickly dissipated. This combination thus yields a good dissolving and absorbable suspension, which in addition does not foam. The suspension was red in color.

EXAMPLE V

A commercial 300 mg capsule of rifampin (Merrell Dow Pharmaceuticals Inc.) was added to 50 ml of Pufified Water USP in a 2 oz prescription bottle, and the bottle was shaken. The capsule dissolved, releasing the rifampin, which resulted in a partially wetted and suspended mixture, which gave copious foaming. The suspension was brown in color.

EXAMPLE VI

A gelatin capsule was filled with the same components as employed in Example IV, and was added to 50 ml of Purified Water as in Example V. The capsule dissolved to release the mixture, which wetted uniformly giving a uniform dispersion, thus enhancing absorbability of the rifampin. After shaking, the mixture had about one-quarter of an inch height of foam on the liquid, far less than the commercial capsule in Example V. The suspension was red in color.

EXAMPLE VII

A commercial 300 mg capsule of rifampin (the same as in Example V) was added to 25 ml of Syrup USP, as recommended in the package insert accompanying the commercial container of the capsules, and 25 ml of Purified Water USP was further added, in a 2 oz prescription bottle. Upon shaking it was found that the rifampin powder did not wet well or form a uniform dispersion. The bottle contained sereral un-wetted lumps on top of the liquid. In addition, about three-quarters of an inch height of foam was formed on top of the suspension, which did not dissipate even after long standing. The suspension was brown in color.

EXAMPLE VIII

A capsule was filled with the same combination of components as described in Example IV. The capsule contents then placed into 25 ml of Syrup USP and 25 ml of Purified Water in a 2 oz prescription bottle and the bottle shaken. The rifampin powder wetted well and formed a uniform dispersion throughout the container. When shaken, the suspension formed about one-quarter of an inch height of foam on the liquid surface, which dissipated within about five minutes. The suspension was red in color.

EXAMPLE IX

A comparative dissolution study was conducted on a commercially available rifampin capsule of the same type employed in Example V (Sample 1), and a capsule prepared according to the procedure of Example VI (Sample 2).

The study was carried out using a USP Dissolution Apparatus 3 (p. 959, USP XX (1980)) with a mixture of 800 ml of Purified Water and 100 ml of Methanol as the dissolution medium, at a temperature of 37 degrees Centigrade.

In each test, a single capsule was added to the apparatus, and the apparatus then turned on.

At various intervals, samples were withdrawn, filtered, and injected into a Waters Reverse Phase HPLC (High Pressure Liquid Chromatograph) L1 Column (Waters Chromatography Division of Millipore Corporation, Milford, Mass.), using as a mobile phase a solution of 68 percent methanol and 32 percent aqueous phosphate buffer having a pH of 6.5. Flow rates in the respective runs of Sample 1 and Sample 2 were each 1 milliliter per minute. In this manner the rifampin in the respective capsules of Samples 1 and 2 was separated and quantified. Results are given below in Table I, in micrograms of rifampin per milliliter of eluate.

TABLE I

| Micrograms of Rifampin per Milliliter of Eluate, for: | Elapsed Elutriation Time, Minutes | | | | | | |
|---|---|---|---|---|---|---|---|
| | 1 | 3 | 5 | 8 | 10 | 15 | 60 |
| Sample 1 | 0 | — | — | 8.9 | 14.8 | 25.3 | 93.4 |
| Sample 2 | — | 99.2 | 197.6 | — | 209.9 | — | 214.1 |

As shown by the data in Table I, the capsule of Sample 2 gave very high initial eluate concentrations due to the uniform homogeneous suspension thereby achieved, as compared to the commercial capsule of Sample 1. Even after an hour of elutriation, the capsule of the present invention gave a rifampin concentration more than twice that achieved by the commercially available capsule of Sample 1.

EXAMPLE X

A liquid syrup suspension of a composition according to the invention was made up, having the formulation set forth below in Table II.

TABLE II

| Component | Concentration |
|---|---|
| Rifampin | 3.3 grams (3.3%) |
| Polysorbate 20 | 0.2 grams (0.2%) |
| Simethicone | 0.15 grams (0.15%) |
| Flavoring[1] | 0.4 milliliters (0.4%) |
| Sucrose | 70.0 grams (70%) |
| Purified Water q.s. | 100.0 milliliters |

[1]Spray dried natural and artificial Fruit Punch Flavor #20337-16 Food Materials Corp. Chicago, Illinois The suspension was made up by first mixing the rifampin with the polysorbate 20 and about 10 milliliters of water, after which 40 milliliters additional water was added, followed by addition of the sucrose, flavoring, and simethicone components, and final dilution, q.s., to 100 milliliters with water, with thorough mixing of all components.

EXAMPLE XI

A powdered mixture of a composition according to the invention was made up, having the formulation indicated in Table III below.

TABLE III

| Component | Concentration |
|---|---|
| Rifampin | 3.0 grams (3.0%) |
| DSS Granular | 0.2 grams (0.2%) |
| Simethicone | 0.1 gram (0.1%) |
| Methylcellulose A4C | 0.1 gram (0.1%) |
| Colloidal Silicon Dioxide | 0.25 gram (0.25%) |

TABLE III-continued

| Component | Concentration |
|---|---|
| Flavoring[1] | 0.4 milliliters (0.4%) |
| Sucrose | 50.0 grams (50.0%) |

[1]Spray dried natural and artificial Fruit Punch Flavor #20337-16 Food Materials Corp., Chicago, Illinois The powdered mixture of the above formulation is suitable for reconstitution by a pharmacist at the time of dispensing. The amounts given in Table III are for one bottle, which when reconstituted by addition of 67 milliliters of water will yield 100 milliliters containing 150 milligrams of rifampin per 5 milliliters of dosage (a teaspoonful).

The powdered mixture formulation of Table III is made up by first mixing the simethicone with the colloidal silicon dioxide, the methylcellulose, the DSS Granular, the flavor, rifampin and sucrose, in that order. The resulting powdered mixture is then packaged in a 4 ounce prescription container.

EXAMPLE XII

The formulation set forth below in Table IV was made up, suitable for usage in solid dosage forms such as capsules or tablets.

TABLE IV

| Component | Concentration |
|---|---|
| Rifampin | 33.0 gram (91.67%) |
| DSS Granular | 1.0 gram (2.78%) |
| Simethicone | 1.3 gram (3.61%) |
| Colloidal Silicon Dioxide | 0.7 gram (1.94%) |

This mixture when utilized in a capsule or tablet dosage form, and administered orally, will wet well, form a smooth suspension providing improved absorption of the active ingredient, and will not foam.

The Table IV formulation is made up by combining the simethicone with the DSS Granular and colloidal silicon dioxide in a mortar and pestle or other suitable mixer, and mixing until a smooth, dry powder is obtained, following which rifampin is mixed into the other components. The resulting powder can be used to fill empty gelatin or soft gelatin capsules, or can be compressed into tablet dosage forms.

Although preferred embodiments of the invention have been described in detail, it will be appreciated that other variations, modifications, and embodiments are contemplated, and accordingly all such variations, modifications and embodiments are to be regarded as being within the spirit and scope of the invention.

What is claimed is:

1. A readily aqueously dispersable antibiotic composition devoid of any enclosing web structure and/or chelating agents, said composition consisting essentially of rifampin, a dimethyl polysiloxane polymer, and a pharmaceutically acceptable cationic or non-ionic surfactant, wherein the rifampin, dimethyl polysiloxane polymer, and pharamceutically acceptable cationic or non-ionic surfactant, are each present in amounts such that the composition is aqueously homogenizable with low foaming incident thereto.

2. A composition according to claim 1, wherein said dimethyl polysiloxane polymer has the formula:

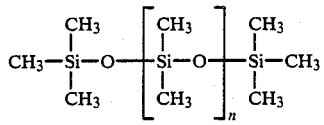

PS wherein n is from about 200 to about 350.

3. A composition according to claim 2, wherein said dimethyl polysiloxane polymer is admixed with a pharmaceutically acceptable silica gel.

4. A composition according to claim 3, wherein said dimethyl polysiloxane polymer and silica gel mixture is simethicone.

5. A composition according to claim 1, wherein said surfactant is a cationic surfactant.

6. A composition according to claim 5, wherein said cationic surfactant is dioctyl sodium sulfosuccinate.

7. A composition according to claim 1, wherein said surfactant is a non-ionic surfactant.

8. A composition according to claim 7, wherein said non-ionic surfactant is polyethylene oxide sorbitan monooleate.

9. A readily aqueously dispersable solid antibiotic composition devoid of any enclosing web structure and/or chelating agents, said composition consisting essentially of a mixture of from about 1 to about 99 percent by weight rifampin, from about 0.05 to about 10 percent by weight of a dimethyl polysiloxane polymer, and from about 0.01 to about 5 percent by weight of a pharmaceutically acceptable cationic or non-ionic surfactant.

10. A composition according to claim 9, in the form of a solid dosage form suitable for oral administration.

11. A composition according to claim 10, in the form of a capsule.

12. A composition according to claim 10, in the form of a tablet.

13. An aqueous dispersion of a composition according to claim 9.

14. An aqueous dispersion according to claim 13, comprising a liquid syrup aqueous medium.

15. A composition according to claim 1, in solid form, and comprising a filler selected from the group consisting of methylcellulose, silica, and mixtures thereof.

16. A composition according to claim 15, containing an amount of methylcellulose which is suspendingly effective for the composition in aqueous medium.

17. A composition according to claim 15, containing silica of submicron particle size, in an amount which is adsorbingly effective for the dimethyl polysiloxane polymer, and is flow improvingly effective for the composition.

18. A method of antibiotic treatment of a mammal, comprising administering an antibiotically effective amount of a composition of claim 1 to said mammal.

19. A method according to claim 18, wherein said composition is in a solid dosage form which is orally administered to said mammal.

20. A method according to claim 18, wherein said composition comprises an aqueous vehicle.

* * * * *